US006977253B2

(12) United States Patent
Kalali et al.

(10) Patent No.: US 6,977,253 B2
(45) Date of Patent: Dec. 20, 2005

(54) METHODS FOR THE TREATMENT OF BIPOLAR DISORDER USING CARBAMAZEPINE

(75) Inventors: Amir H. Kalali, San Diego, CA (US); Simon J. Tulloch, Gaithersburg, MD (US)

(73) Assignee: Shire Pharmaceutical Development Inc., Rockville, MD (US)

( * ) Notice: Subject to any disclaimer, the term of this patent is extended or adjusted under 35 U.S.C. 154(b) by 0 days.

(21) Appl. No.: 10/848,383

(22) Filed: May 19, 2004

(65) Prior Publication Data

US 2005/0124601 A1 Jun. 9, 2005

Related U.S. Application Data

(60) Provisional application No. 60/527,298, filed on Dec. 8, 2003.

(51) Int. Cl.$^7$ .............................................. A61K 31/55
(52) U.S. Cl. ...................................... 514/217; 514/212
(58) Field of Search ................................. 514/217, 212

(56) References Cited

U.S. PATENT DOCUMENTS

| 2,948,718 A | 8/1960 | Schindler et al. |
| 5,326,570 A | 7/1994 | Rudnic et al. |
| 5,912,013 A | 6/1999 | Rudnic et al. |

FOREIGN PATENT DOCUMENTS

| EP | 0 029 409 | 5/1981 |
| EP | 0 277 095 | 8/1988 |
| EP | 0 423 679 | 4/1991 |
| EP | 0 485 685 | 5/1992 |
| EP | 0 688 768 | 12/1995 |

OTHER PUBLICATIONS

Simhandl et al. The comparative efficacy of carbamazepine low and igh serum level and lithium carbonate in the propylaxis of affective disorders. Journal of Affective Disorders, 28 (1993) pp. 221-231.*
The use of carbamazepine (Tegretol) in the control of manic-depressive psychosis and other manic, depressive states, Takezaki H and Hanaoka M. Clinical Psychiatry 1971; 13: 173-183.
"Anti-Manic and Prophylactic Effects of Carbamazepine (Tegretol) on Manic Depressive Psychosis", Teruo Okuma et al., Folia Psychiatrica et Neurologica Japonica, vol. 27, No. 4, (1973).
"Comparison of the Antimanic Efficacy of Carbamazepine and Chlorpromazine: A Double-Blind Controlled Study", Teruo Okuma et al., Psychopharmacology 66, 211-217 (1979).
Carbamazepine vs Chlorpromazepine in Mania: A Double Blind Trial, 1984 Elsevier Science Publishers B.V., Anticonvulsants in affective disorders, E. Grossi et al.

Carbamazepine Versus Lithium in Mania: A Double-Blind Study, Bernard Lerer et al., J. Clin. Psychiatry 48:3, Mar. 1987.
"Comparison of the Antimanic Efficacy of Carbamazepine and Lithium Carbonate by Double-Blind Controlled Study", T. Okuma et al., Pharmacopsychiatry 23 (1990) 143-150.
"NCDEU Updates", "Anticonvulsants in affective Disorders", Joyce G. Small, Psychopharmacology Bulletin, vol. 26, No. 1, 25-36, 1990.
"Carbamazepine Compared With Lithium in the Treatment of Mania", Joyce G. Small et al., Arch Gen Psychiatry—vol. 48, Oct. 1991.
"Carbamazepine and its 10,11-epoxide metabolite in acute mania: clinicaland pharmacokinetic correlates", P. Petit et al., Eur. J. Clin. Pharmacol (1991) 41:541-546.
"Carbamazepine Expoxide" Bradley M. Kerr and René H. Levy, Antiepileptic Drugs, Fourth Edition, edited by R.H. Levy, R.H. Mattson and B.S. Meldrum, Raven Press Ltd 1995, 529-541.
"Carbamazepine Chemistry and Biotransformation", Johann W. Faigle and Karl F. Feldmann, Antiepileptic Drugs, Fourth Edition, edited by R.H. Levy, R.H. Mattson and B.S. Meldrum, Raven Press, Ltd. New York 1995, 499-513.
"Dosing Strategies and Time Course of Response to Antimanic Drugs", Charles L. Bowden, J. Clin. Psychiatry 1996;57 (suppl 13).
"Corrections", in the Article "Rapid Titration of Mood Stabilizers Predicts Remission From Mixed or Pure Mania in Bipolar Patients", Joseph F. Goldberg et al., J. Clin. Psychiatry 1998; 59:6, 320.
"Rapid Titration of Mood Stabilizers Predicts Remission From Mixed or Pure Mania in Bipolar Patients", Joseph F. Goldberg et al., J. Clin. Psychiatry 59:4, Apr. 1998, 151-158.
"Pharmacokinetic Evaluation of Twice-Daily Extended-Release Carbamazepine (CBZ) and Four-Times-Daily Immediate-Release CBZ in Patients with Epilepsy", William R. Garnett et al., Epilepsia, 39(3):274-279, 1998.
"Controlled Multidose, Pharmacokinetic Evaluation of Two Extended-Release Carbamazepine Formulations (Carbatrol and Tegretol-XR)", Ruth E. Stevens et al. Journal of Pharmaceutical Sciences, vol. 87, No. 12, Dec. 1998.
"Six-month evaluation of Carbatrol (extended-release carbamazepine) in complex partial seizures", W.U. Mirza et al. Neurology, 19; 1727-1729, 1998.

(Continued)

Primary Examiner—Sreenivasan Padmanabhan
Assistant Examiner—Jennifer Kim
(74) Attorney, Agent, or Firm—Millen, White, Zelano, Branigan, P.C.

(57) ABSTRACT

Carbamazepine, in extended release form, is useful in the treatment of patients suffering from bipolar disorder. In order to minimize the time it takes to reach efficacy, carbamazepine, in extended release form, can be administered to the patient at an initial daily dose which is then increased in daily increments until clinical efficacy is achieved.

34 Claims, 3 Drawing Sheets

OTHER PUBLICATIONS

"Anticonvulsants and Antipsychotics in the Tratment of Bipolar Disorder", Paul E. Keck et al., . Clin, Psychiatry 1998;59 (suppl 6).

"New formulations of drugs in epilepsy", James W. Wheless et al., *Exp. Opin, Pharmacother.* (1999) 1(1):49-60.

"Gastrointestinal performance of the Microtrol extended release drug delivery technology", P H Hirst et al., Proceed. Int'l Symp. Control. Rel. Bioact. Mater., 26(Revised Jul. 1999) Controlled Release Society, Inc.

"Carbamazepine and valproate monotherapy: feasibility, relative safety and efficacy, and therapeutic drug monitoring in manic disorder", Kamini Vasudev et al., Psychopharmacology (2000) 150:15-23.

"Extended Release Formulations of Anticonvulsant Medications", Rebeccah J. Collins et al., *CNS Drugs* 2000 Sep. 14(3):203-212.

"The Influence of Food on the Bioavailability of a Twice-Daily Controlled Release Carbamazepine Formulation", Angus McLean et al. *J. Clin. Pharmacol* . 2001 ; 41:183-186.

"Extended Release Carbamazepine: Optimizing Epilepsy Treatment", Carbatrol "Extended Release Carbamazepine Capsules" Scientific Exhibit, Dec. 9, 2002, 2002 American Epilepsy Society Annual Meeting, Room 615.

"Open-Label, 6-Mont h Evaluation of the Safety and Efficacy of Extended-Release Carbamazepine Capsules (Carbatrol®) in Patients with Manic or Mixed Bipolar Disorder", Terence A. Ketter et al., poster Dec. 9, 2002, 2002 American Epilepsy Society Annual Meeting.

"Reanalysis of Carbamazepine and Carbamazepine-Epoxide Pharmacokinetics after Multiple Dosing of Extended Release Formulations", David H. Mason et al., *J. Pharm. Parmaceut Sci.* 5(2):169-175, 2002.

"Administration of Carbatrol to Children With Feeding Tubes", Jennifer R. Riss et al., Elsevier Science 2002.

"Open-Label, 6-Month Evaluation of the Safety and Efficacy of Extended-Release Carbamazepine Capsules (Carbatrol®) in Patients with Manic or Mixed Bipolar Disorder", Terence A. Ketter, poster presented Dec. 9, 2002, at American Epilepsy Society 56th Annual Meeting, Dec. 6-11, 2002, Seattle, Washington.

"A Multicenter, Ramdomized, Double-Blind, Placebo-Controlled Trial of Extended-Release Carbamazepine Capsules (Carbatrol®) Monotherapy in Patients with Mania or Mixed Bipolar Disorders," by R.H. Weisler, poster presented Dec. 9, 2002 at American Epilepsy Society 56th Annual Meeting, Dec. 6-11, 2002, Seattle, Washington.

"Extended-Release Carbamazepine (Carbatrol®) in Bipolar Disorders: A 6 Month Open-Trial," by Mark B. Hamner and Terrence, A. Ketter, poster presented at APA 2003 American Psychiatric Association 156th Annual Meeting, May 17-22, 2003, San Francisco, California (Abstract NR491. p. 184).

"A 3-Week, Double-Blind, Placebo-Controlled Study of Extended-Release Carbamazepine in the Treatment of Acute Mania in Bipolar Disorders," by A. H. Kalali, T. A. Ketter, and R. H. Weisler, poster presented at NCDEU 2003 43rd Annual New Clinical Drug Evaluation Unit (NCDEU) Meeting, May 26-28, 2003, Boca Raton, FL.

"Extended-Release Carbamazepine in Bipolar Disorders," by T. A. Ketter, R. H. Weisler, and A. H. Kalali, poster presented at ICBD 2003 Fifth International Conference on Bipolar Disorder, Jun. 12-14, 2003, Pittsburgh, Pennsylvania.

"Open-Label, 6-Month Evaluation of the Safety and Efficacy of SPD-417 (Beaded, ERC-CBZ) in Patients with Manic or Mixed Bipolar Disorder", Terence A. Ketter and Sherry L. Andes, poster presented at the meeting of American College of Clinical Pharmacy, Atlanta, Nov. 2-5, 2003.

"A Multicenter, Randomized, Double-Blind, Placebo-Controlled Trial of SPD-417 (Beaded, ERC-Carbamazepine) Monotherapy in Patients with Mania or Mixed Bipolar Disorders," R. H. Weisler and Sherry L. Andes, poster presented at the meeting of American College of Clinical Pharmacy, Atlanta, Nov. 2-5, 2003.

"Extended-Release Carbamazepine (Carbatrol©) in Bipolar Disorders: A 6 Month Open-Trial," by Mark B. Hamner and Terrence. A. Ketter, poster presented at USPsych 2003 16th Annual Psychiatric & Mental Health Congress, Orlando, Nov. 6-9, 2003.

A 3-Week, Double-Blind, Placebo-Controlled Study of Extended-Release Carbamazepine in the Treatment of Acute Mania in Bipolar Disorders, by A. H. Kalali, T. A. Ketter, and R. H. Weisler, poster presented at USPsych 2003 16th Annual Psychiatric & Mental Health Congress, Orlando, Nov. 6-9, 2003.

"Bipolar Disorder—A Practical Guide to Drug Treatment", Michael Bauer and Bernd Ahrens. CNS Drugs 1996 V.6(1) p. 35-52.

Comparative prophylactic efficacy of lithium, carbamazepine and the combination in bipolar disorder. Kirk D. Denicoff et al. 1997 V.58(11) p470-478.

"Management of Acute Mania", Mauricio-Tohen, et al. Journal of Clinical Psychiatry, 1999 V.60 Suppl 5 p31-34, Tohen M. Grundy S.

"Pharmacologic Agents for the Treatment of Acute Bipolar Mania", Susan L. McElroy and Paul E. Keek, Jr. Biological Chemistry Hoppe-Seyler, 2000 V.48(6) p539-557.

"Perspectives on the use of anticonvulsants in the treatment of bipolar disorder". Brambilia P. Barale F. Soares JC, 2001 V.4(4) p421-446.

"Carbamazepine and Valproate in the Maintenance Treatment of Bipolar Disorder", Paul E. Keck, Jr., M.D., and Susan L. McElroy, M.D., J. Clin. Psychiatry 2002; 63 (suppl 10).

"Clinical Pharmacodynamics and Pharmacokinetics of antimanic and Mood-Stabilizing Medications", Paul E. Keck, Jr., M.D., and Susan L. McElroy, M.D., J. Clin. Psychiatry 2002;63 (suppl 4).

"Psychopharmacological treatment with lithium and antiepileptic drugs: suggested guidelines from the Danish Psychiatric Association and the Child and Adolescent psychiatric Association in Denmark", R.W. Licht et al. Acta Psychiatra Scandinavica, Supplementum (2003), 419 1-22.

"Efficacy of newer anticonvulsant medications in bipolar spectrum mood disorders", Evins, A. Eden. Journal of Clinical Psychiatry (2003), 64(Suppl. 8), 9-14.

"Mood stabilizers in hospitalised children with bipolar disorder: a retrospective review", Pablo Davanzo et al. Psychiatry and Clinical Neurosciences (2003), 57(5), 504-510.

"Acute and maintenance treatment with mood stabilizers", Charles L. Bowden, International Journal of Neuropsychopharmacology (2003), 63(3), 269-273.

"Prophylactic efficacy of lithium versus carbamazepine in treatment-naive bipolar patients", Erwin G. Th. M. Hartong et al. Journal of Clinical Psychiatry (2003), 64(2), 144-151.

"Antidepressant properties of anticonvulsant drugs for bipolar disorder", Carrie L. Ernst, M.D. and Joseph F. Goldberg, M.D., Journal of Clinical Psychopharmacology (2003), 23(2), 182-192.

"Correlates of Antimanic Response to Carbamazepine", Robert M. Post, et al., Elsevier Science Publishers (1987) Psychiatry Research (21), 71-83.

* cited by examiner

Figure 1. Mean YMRS total scores for extended-release carbamazepine patients (ITT population)
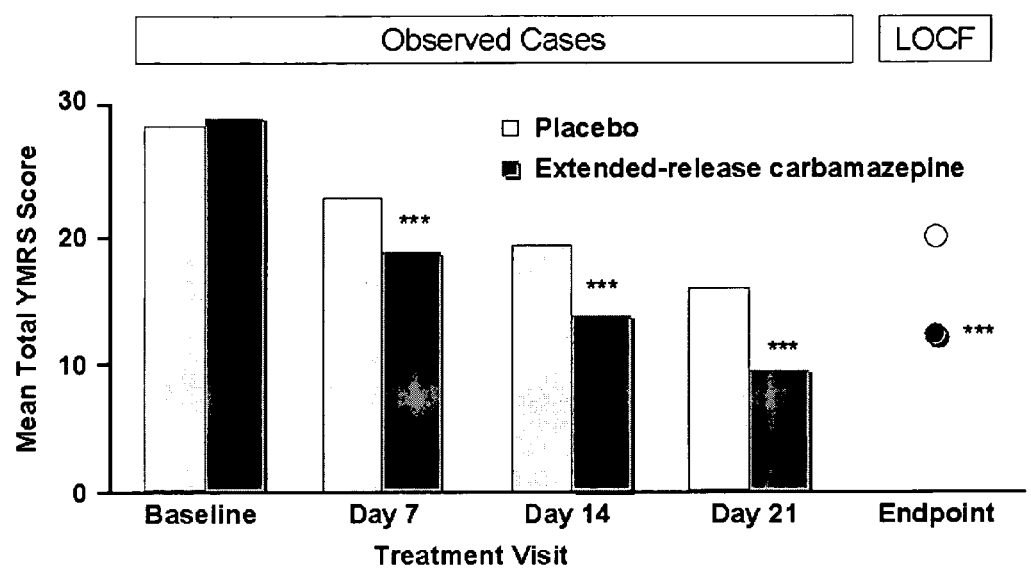
***$P < .001$ compared to placebo following ANCOVA with baseline score as covariate.
Data on file, Shire Pharmaceutical Development.

Figure 2. Increased percent responders (>50% YMRS) on extended-release carbamazepine (ITT population)
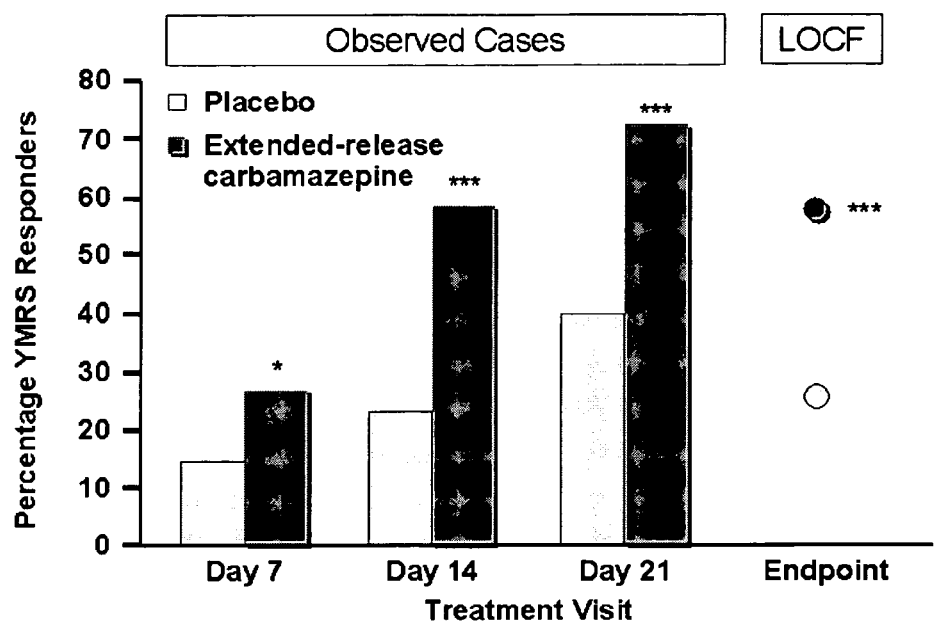
*$P = .0286$, ***$P < .001$ compared to placebo following ANCOVA with baseline score as covariate. Data on file, Shire Pharmaceutical Development.

Figure 3. Significant reduction in HAM-D score on extended-release carbamazepine (ITT population)
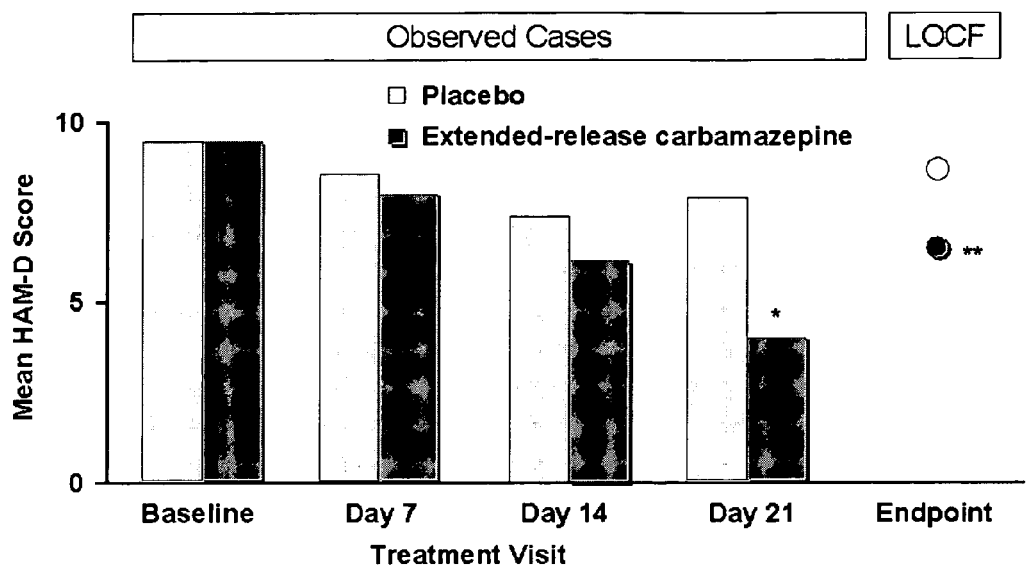
*$P$ = .002, **$P$ = .008 compared to placebo following ANCOVA with baseline score as covariate.
Data on file, Shire Pharmaceutical Development.

METHODS FOR THE TREATMENT OF BIPOLAR DISORDER USING CARBAMAZEPINE

This application claims the benefit of U.S. provisional patent application Ser. No. 60/527,298, filed Dec. 8, 2003.

FIELD OF THE INVENTION

The present invention relates to methods of treating bipolar disorder in patients using extended release formulations of carbamazepine wherein the dosage regimen has an initial rapid titration period.

BACKGROUND OF THE INVENTION

Carbamazepine, or 5-carbamoyl-5H-dibenz(b,f)azepine (or 5H-dibenz(b,f)azepine-5-carboxamide or N-carbamoyliminostilbene), is an iminostilbene derivative which is a known analgesic and anticonvulsant used for the treatment of epilepsy, the pain associated with trigeminal neuralgia, psychomotor and grand mal seizures, and neurological disorders such as chronic pain states and headaches. Additionally, carbamazepine is used in various psychiatric disorders such as bipolar disorder, depression, cocaine addiction, alcohol addiction, opiate addiction, nicotine addiction, other obsessive compulsive disorders and cardiovascular disease.

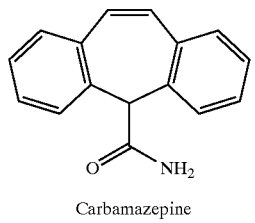

Carbamazepine

Carbamazepine and its synthesis are described in U.S. Pat. No. 2,948,718. Other processes for synthesizing carbamazepine are described in EP 0 029 409, EP 0 277 095, EP 0 688 768, EP 0 423 679, and EP 0 485 685.

Carbamazepine extended-release formulations have been developed in recent years to decrease daily fluctuations in serum carbamazepine concentration by smoothing out bloods levels of the drug and to improve dosing convenience. These extended-release formulations are typically designed to provide carbamazepine at a therapeutic range of from about 4 µg/ml to about 12 µg/ml of carbamazepine over a period of time. Blood levels of carbamazepine of less than 4 µg/ml have been found to be ineffective in treating clinical disorders while blood levels greater than 12 µg/ml have been found to be likely to result in undesirable side effects such as neuromuscular disturbances, cardiovascular and gastrointestinal effects.

SPD417 and Carbatrol® (both from Shire US Inc., Newport, Ky.) are extended-release preparations of carbamazepine which has allowed for twice daily administration of the drug in patients (See U.S. Pat. No. 5,326,570 and U.S. Pat. No. 5,912,013 which describe the formulation of carbamazepine). Currently, Carbatrol® is approved by the FDA for use in the treatment of epilepsy and pain associated with trigeminal neuralgia. For treating epilepsy, the usual initial dose for adults and children over 12 years of age is 200 mg taken twice daily. The dosage is then increased at weekly intervals by adding 200 mg/day. The dosage should generally not exceed 1,000 mg daily in children 12 to 15 years old and 1,200 mg daily for adults and children over 15 (dosages up to 1600 mg daily have been used for adults. For maintenance, the daily dosage is generally 800 to 1,200 mg. For treating trigeminal neuralgia, the usual dose is 200 mg on the first day and may be increased by up 200 mg every 12 hours as needed to achieve freedom from pain. The doses should not exceed 1,200 mg daily and the maintenance dose is usually in the range of 400 mg to 800 mg.

Tegretrol-XR® is another extended release, oral formulation of carbamazepine (sold by Novartis Pharmaceuticals) which is approved by the FDA for the treatment of epilepsy and the pain associated with trigeminal neuralgia. The suggested dosage regimens for Tegretrol-XR® are the same as for the Carbatrol® extended release formulation.

The range of therapeutic options for bipolar disorder has included in recent years several anticonvulsants and antipsychotic medications. Carbamazepine, a major antiepileptic drug used in treating convulsive, simple and complex partial seizures, has also long been considered one of the standard therapies for bipolar disorder, although it is not approved for this use by the FDA (drugs currently approved by FDA for the treatment of acute mania include lithium, valproate, chlorpromazine, olanzapine and lamotrigine). See, e.g., Okuma et al., "Anti-Manic and Prophylactic Effects of Carbamazepine (Tegretol®) on Manic Depressive Psychosis," Folia Psychiatrica et Neurologica Japonica, 27:4, pp. 283–297 (1973); Okuma et al., "Comparison of the Antimanic Efficacy of Carbamazepine and Chlorpromazine in Mania: A Double-Blind Trial," Psychopharmacology, 66, pp. 211–217 (1979); Grossi et al., "Carbamazepine vs Chlorpromazine: A Double-Blind Controlled Study," in: Emrich et al. (eds) Anticonvulsants in Affective Disorders, Princeton, N.J., Excerpta Medica, pp. 177–187 (1984); Lerer et al, "Carbamazepine Versus Lithium in Mania: A Double-Blind Study," J. Clin. Psychiatry, 48:3, pp. 89–93 (1987); Okuma et al., "Comparison of the Antimanic Efficacy of Carbamazepine and Lithium Carbonate by Double-Blind Controlled Study," Pharmacopsychiatry, 23, pp. 143–150 (1990); and Keck et al., "Carbamazepine and Valporate in the Maintenance Treatment of Bipolar Disorder," J. Clin. Psychiatry, 63 (Suppl 10), pp. 13–17 (2002).

However, in the treatment of bipolar disorder, carbamazepine has been used mainly in immediate-release preparations which need to be administered three or four times daily to avoid potentially problematic serum drug fluctuations. Also, in these treatments, carbamazepine has generally been administered at a constant dosage (see, e.g., Okuma et al. (1973)), at an initial constant dosage with subsequent adjustment (see, Okuma et al. (1979)), or at a gradually increasing dosage (See, e.g., Lerer et al. (1987)).

As described above, the generally accepted method for administering extended-release carbamazepine in the treatment of epilepsy has been to initiate a patient with 200 mg/day twice daily of carbamazepine with weekly increases of up to 200 mg/day until the optimal response was obtained. This dosage regime has also been used for the treatment of bipolar disease. Despite the treatments which are presently available with carbamazepine, there is a need to treat bipolar disorder using a more rapid treatment period than that which has been previously used.

Goldberg et al. [J. Clin. Psychiatry, 59:4, pp. 151–158, April 1998] reports the results of a retrospective study comparing the time to remission for pure and mixed manic bipolar patients who were treated with lithium, carbamazepine, divalproex, or combinations thereof. Of the 120 subjects included in this study, only 7 subjects took carbamazepine alone (4 mixed manic; 3 pure manic). Goldberg et al. conclude that the time course to remission "appears to be strongly influenced by the speed which patients achieve a therapeutic serum level of an antimanic agent." In the study, the minimum therapeutic serum level for carbamazepine was ≧8 µg/mL. Goldberg et al. do not describe the dosage regimens used in the study for administering carbamazepine.

Vasudev et al. [Psychopharmacology, 150:15–23 (2000)] report the results of a study comparing carbamazepine and valproate monotherapies. In the study, carbamazepine was given orally in the form of 200 mg tablets. The subjects treated with carbamazepine were initially given 400 mg/day in two divided doses. The dose was then increased by 200 mg/day or 400 mg/day for the next two days. Thereafter, the dose was increased 200–400 mg at weekly intervals. This was continued until clinical improvement occurred, or a serum level not exceeding 14 µg/ml was reached, or dose limiting adverse effects occurred. The therapeutic serum level window used in the study for carbamazepine was 6–12 µg/ml. In the study, favorable clinical responses were considered responses that showed a more than 50% fall in YMRS scores from baseline. Vasudev et al. conclude from the results of the study that both carbamazepine and valproate monotherapies are feasible but the valproate monotherapy is more efficacious.

Bipolar disorder is a brain disorder which causes unusual shifts in a person's mood, energy and ability to function. The symptoms of bipolar are quite severe and can even result in suicide. Therefore, there remains a need for methods of treating bipolar disorder with carbamazepine that provide efficacy while minimizing the time it takes for the patient to reach efficacy and thus providing an effective method of treating bipolar disorder.

SUMMARY OF THE INVENTION

In accordance with the invention, there is provided a method of treating a patient suffering from bipolar disorder wherein the patient is administered an initial dosage of carbamazepine, in an extended release formulation, and then the dosage is titrated, specifically increased by daily increments, until clinical efficacy is achieved. Thereafter, the patient can be given a daily maintenance dosage which is the same or about the same as the final dosage at the end of the titration period or is a lower daily dosage.

According to an embodiment of the invention, there is provided a method which comprises administering to a bipolar patient an initial daily dose of carbamazepine (e.g., 400 mg) in extended release form and then increasing the dose by daily increments (e.g., 200 mg/day) until clinical efficacy is achieved.

According to another embodiment of the invention, there is provided a method which comprises administering to a patient suffering from bipolar disorder an initial daily dose of carbamazepine in extended release form and increasing the dose by daily increments until clinical efficacy is achieved, wherein the occurrence of adverse side effects is not greater than that which occurs when the daily dose is increased in weekly increments.

According to a further embodiment of the invention, there is provided a method for treating a patient suffering from bipolar disorder comprising administering to the patient an initial daily dose of 100–800 mg carbamazepine in extended release form and increasing the daily dose by increments of 100–400 mg until clinical efficacy is achieved. Total daily dose should, preferably, not exceed 1,600 mg.

According to another aspect of the invention, the titration period, which includes the initial daily dose, is at least 5 days, preferably at least 6 days, especially at least 7 days. For example, clinical efficacy is achieved after at least 7 days, that is the period of time during which the daily dose is increased by increments is at least 6 days.

According to another aspect of the invention, after clinical efficacy is achieved, the treatment is continued by administering to the patient the same daily dose as at which clinically efficacy was achieved or by reducing the daily dose, for example, by daily increments to a dosage level which is lower than that at which clinical efficacy was achieved, whereby efficacy can be maintained. According to a further aspect of the invention, the maintenance dosage following the titration period is 100–1600 mg/day, for example, 800–1,000 mg/day.

The methods according to the invention can be used to treat patients with bipolar disorder who experience manic episodes and/or mixed episodes. Furthermore, the methods can be used to treat patients with bipolar disorder II.

As used in this application, the term "bipolar disorder" represents a disorder which causes dramatic mood swings, from episodes of mania to depression. Bipolar disorder represents manic-depressive disorder, bipolar disorder I (symptoms include alternating episodes of mania and depression), bipolar disorder II (symptoms include alternating hypomanic and depressive episodes), rapid-cycling bipolar disorder (occurs when four or more episodes of illness occur within a 12 month period in a patient) and all other types of depressive and mood disorders that are well known by those of skill in the art.

In accordance with an aspect of the methods of the invention, carbamazepine is preferably administered twice daily. The initial daily dose is, for example, 200 mg, 400 mg, 600 mg or 800 mg, preferably 400 mg. During the titration period, the daily incremental increase in daily dose is, for example, 100 mg, 200 mg, 300 mg or 400 mg, preferably 200 mg.

In accordance with an aspect of the methods of the invention, carbamazepine is preferably administered once daily. The initial daily dose is, for example, 100 mg, 200 mg, 300 mg or 400 mg. During the titration period, the daily incremental increase in daily dose is, for example, 100 mg, 200 mg, 300 mg or 400 mg.

In accordance with the present invention, extended release formulations of carbamazepine can be administered sublingually, transmucosally, transdermally, parenterally and orally. Suitable dosage forms include but are not limited to liquids, tablets, capsules, sprinkle dosage forms, chewable tablets, pellets and transdermal patches. Oral administration is preferred, preferably in the form of capsules, such as described in U.S. Pat. No. 5,326,570 and U.S. Pat. No. 5,912,013, which are hereby incorporated by reference.

In the context of the invention, evaluation of efficacy can be performed by use of the Young Mania Rating Scale (YMRS). On this scale, normalcy is associated with a rating of approximately 5 to 10. A rating above 20 is considered to be indicative of abnormalcy. Thus, using this scale, clinical efficacy occurs when there is at least a 50% reduction in a YMRS score from the baseline determined prior to the initiation of dosing.

It is to be understood that other means could be used for determining clinical efficacy, such as CGI (clinical global impression scale). Another endpoint for efficacy which could be used in patients that have depressive symptoms is HDRS (or HAM-D).

In accordance with the invention, carbamazepine can be used as a monotherapy for treating bipolar disorder. Alternatively, the inventive method can be used in conjunction with treatments that use other agents such as lithium, valproate, chlorpromazine, olanzapine, lamotrigine, and gabapentin.

The entire disclosures of all applications, patents and publications cited above are hereby incorporated by reference.

EXAMPLE 1

A multicenter, placebo-controlled, double-blind, randomized clinical trial was conducted to evaluate the efficacy and safety of monotherapy with extended-release carbamazepine capsules (SPD417, supplied by Shire US Inc., Newport, Ky.) in bipolar disorder patients with manic and mixed episodes.

Subjects

The subjects enrolled in this study were at least 18 years of age and met DSM-IV criteria for bipolar I disorder with most recent manic or mixed episodes. A history of at least 1 previous manic or mixed episode and minimum screen and baseline total score of 20 on the Young Mania Rating Scale (YMRS) was required, as per the YMRS rating scale reported in Young R C, Biggs J T, Ziegler V E, et al., *Br J Psychiatry*, 1978; 133: 429–435. The patients were not eligible to enroll in this study if they had been treated with electroconvulsive therapy (ECT) or clozapine within 3 months of baseline or antidepressants within 4 weeks of baseline. Concomitant therapy with antidepressants, antipsychotics, lithium, ECT, or anxiolytic or sedative-hypnotic drugs was prohibited, with the exception of lorazepam which may have been used for agitation or sleep.

Methods

A 21-day randomized, double-blind, placebo-controlled study was conducted followed by a 5-day single-blind placebo lead-in period. Treatment with extended-release carbamazepine was initiated at 200 mg twice a day and titrated by increments of 200 mg/day to final doses between 200 mg/day and 1600 mg/day, as necessary and tolerated. Efficacy was assessed weekly with the YMRS, Clinical Global Impression (CGI) scales, Hamilton Depression Rating Scale (HAM-D or HDRS). Each week, adverse events (AEs) and compliance was recorded. The primary efficacy outcome measure was the change from baseline to last observation in the YMRS total score. Secondary efficacy assessments included responder rate (percentage of patients with at least a 50% decrease in YMRS scores from baseline to last observation), change from baseline to last observation in Clinical Global Impression (CGI) and in the 21-Item Hamilton Rating Scale for Depression (HAM-D), depressed mood item score, and time-to-outpatient status.

Data Analysis

All statistical analyses were carried out using SAS windows (version 8.0). SAS Type III estimation was utilized, and the significance level was set at 0.05 for all statistical tests. The primary efficacy end point was the last observation carried forward (LOCF) value of the decrease from baseline in YMRS total score at day 21 of double-blind treatment for the intent-to-treat (ITT) population. The YMRS total score, HAM-D total score, HAM-D depressed mood item score, and CGI severity score at each post-randomization visit and endpoint were analyzed using a two-way analysis of covariance (ANCOVA) model with treatment and site as the main factors and the baseline value as the covariate for the ITT population. A two-way analysis of variance (ANOVA) was performed on baseline data for these variables with treatment and site as the main factors. The number of subjects with a CGI improvement score, the number of subjects demonstrating a response at each post-randomization visit (Days 7, 14, and 21), and the number of subjects showing a sustained response were analyzed using the Chi-square test with continuity adjustment. Fisher's exact test was used to compare AEs of incidence greater than or equal to 1% between treatment groups.

Results

At 25 study sites, 239 patients were randomized to double-blind treatment, and 144 completed the study. Early discontinuation rates were not significantly different and reasons for the discontinuations were similar between the two treatment groups. There were no important differences between the treatment groups in any demographic and disease diagnosis characteristics at baseline in the randomized subjects and the ITT population. It is to be noted that in the present study, in the diagnosis of the recent bipolar disorder, more subjects had manic bipolar disorder (that is, 79% manic vs. 21% mixed mania).

Treatment-Emergent AEs

As can be seen in Table 1, the most frequently reported treatment emergent serious AEs in the extended-release carbamazepine group were dizziness (39.3%), somnolence (30.3%), and nausea (23.8%). Adverse events reported in this study were typical of those reported in previous trials of carbamazepine in epilepsy and bipolar disorder. The incidence of serious adverse events (SAEs) was similar between the two treatment groups (extended-release carbamazepine: four subjects, six events; placebo: six subjects, six events). Of the ten subjects who experienced a SAE during the double-blind treatment period, seven subjects (three extended-release carbamazepine and four placebo) discontinued the study due to a SAE.

Final Daily Dose of Study Medication

From the 235 ITT subjects of this study, 4.7% had a final daily dose of extended-release carbamazepine of 200 mg, 30.6% had a final daily dose of 400–600 mg, 38.7% had final daily dose of 800–1000 mg, 6.4% had a final daily dose of 1200–1400 mg, and 19.6% had a final daily dose of 1600 mg. Most placebo subjects had a final daily dose of 800–1000 mg (53.9%) or 1600 mg (29.6%).

Efficacy

As can be seen in FIG. 1, the patients treated with extended-release carbamazepine had significantly greater decreases in YMRS total scores compared to patients receiving placebo beginning at week 1 and at primary end point, day 21. In this study, day 7 was the first time point at which efficacy measures were performed, and this early improvement can be compared to results from trials of atypical antipsychotic medications in acute mania.

Surprisingly, the treatment regimen as conducted in the present study (initially 200 mg twice a day and titrated by increments of 200 mg/day to final doses between 200 mg/day and 1600 mg/day) enabled the patients to achieve significant improvements in YMRS and CGI scores beginning on day 7.

FIG. 2 depicts YMRS response rates (patients showing a decrease in YMRS total score of at least 50%) at different time points during the study. Patients treated with extended-release carbamazepine had significantly higher response rates than patients treated with placebo at day 7 (P=0.0286), day 14 day 21 (P<0.0001), and endpoint (P<0.0001). Compared to placebo, extended-release carbamazepine treatment was associated with significantly improved scores on both the CGI improvement and CGI severity scales at day 7 (both P<0.01), as well as on days 14, 21 and at endpoint (all P<0.0001), using LOCF analysis.

It can be seen from FIG. 2, that at end point (Day 14), 60.8% of extended-release carbamazepine-treated patients were considered YMRS responders (vs. 28.7% with placebo; P<0.0001). In a review of controlled carbamazepine monotherapy trials in acute mania, the pooled response rate was reported to be 52%. Reference: McElroy S L, Keck P E, Jr. Pharmacologic agents for the treatment of acute bipolar mania. Biol Psychiatry 2000; 48: 539–557

HAM-D total score, as can be seen in FIG. 3, was also significantly improved in extended-release carbamazepine-treated patients compared to placebo-treated patients both on day 21 (P=0.002) and at endpoint (P=0.008). At day 21, although only a small group of patients were evaluated for depressive symptoms, the results are statistically significant in showing that the depressive symptoms were subsiding with the extended-release carbamazepine.

The results indicate that monotherapy with extended-release carbamazepine capsules was effective and safe for the treatment of bipolar patients with manic or mixed episodes in this multicenter, randomized, double-blind, placebo-controlled trial. Patients treated with extended-release carbamazepine had significantly greater improvements on the YMRS, CGI-I, CGI-S, and HAM-D scales than those treated with placebo. The above-results show for the first time in a placebo-controlled study that extended-release carbamazepine administered in a daily dosing schedule produces clinical improvement with satisfactory tolerability and safety in patients with bipolar disorder.

EXAMPLE 2

A similar dosing regimen could be used for conducting a study of efficacy and safety of monotherapy with extended-release carbamazepine in bipolar disorder patients with manic and mixed episodes by administering the drug 100 mg to 400 mg once a day and titrated in increments of 100 to 400 mg/day to final doses between 100 mg/day and 1600 mg/day, as necessary and tolerated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

TABLE 1

Notable Treatment-Emergent Adverse Events*

| AEs | Extended-release carbamazepine (n = 122) n (%) | Placebo (n = 117) n (%) |
|---|---|---|
| Any[†] | 112 (91.8) | 66 (56.4) |
| Dizziness[†] | 48 (39.3) | 14 (12.0) |
| Somnolence[†] | 37 (30.3) | 12 (10.3) |
| Nausea[†] | 29 (23.8) | 11 (9.4) |
| Headache | 25 (20.5) | 15 (12.8) |
| Ataxia[†] | 23 (18.9) | 0 |
| Vomiting[†] | 20 (16.4) | 3 (2.6) |
| Dyspepsia | 16 (13.1) | 13 (11.1) |
| Blurred Vision[†] | 11 (9.0) | 2 (1.7) |
| Pain | 9 (7.4) | 12 (10.3) |

*Treatment-emergent adverse events reported by more than 10% of patients in either treatment group or significantly different between treatment groups.
[†]Treatment-emergent adverse events with a significant difference between treatment groups

What is claimed is:

1. A method of treating a patient suffering from bipolar disorder comprising administering to said patient an initial daily dose of 100–800 mg of carbamazepine in extended release form and increasing said dose by daily increments of 100–400 mg until clinical efficacy is achieved, wherein the occurrence of adverse side effects is not greater than that which occurs when the daily dose is increased in weekly increments.

2. A method of treating a patient suffering from bipolar disorder comprising administering to said patient an initial daily dose of 100–800 mg carbamazepine in extended release form and increasing said daily dose by daily increments of 100–400 mg until clinical efficacy is achieved.

3. A method according to claim 2, wherein said method is used to treat a patient that suffers from manic episodes.

4. A method according to claim 2, wherein said method is used to treat a patient that suffers from mixed episodes.

5. A method according to claim 2, wherein carbamazepine is administered twice daily.

6. A method according to claim 2, wherein said initial dose is 200 mg.

7. A method according to claim 2, wherein said initial dose is 400 mg.

8. A method according to claim 2, wherein said initial dose is 600 mg.

9. A method according to claim 2, wherein said initial dose is 800 mg.

10. A method according to claim 2, wherein the daily dose increment is 100 mg.

11. A method according to claim 2, wherein the daily dose increment is 200 mg.

12. A method according to claim 2, wherein the daily dose increment is 300 mg.

13. A method according to claim 2, wherein the daily dose increment is 400 mg.

14. A method according to claim 2, further comprising administering to said patient lithium, valproate, chlorpromazine, olanzapine, lamotrigine, gabapentin or a combination thereof.

15. A method according to claim 1, wherein the period of time during which the daily dose is increased daily by increments is at least 6 days.

16. A method according to claim 1, further comprising continuing to treat said patient by administering the same daily dose as at which clinically efficacy is achieved or reducing said daily dose by daily increments to a lower level at which efficacy can be maintained.

17. A method according to claim 2, wherein the period of time during which the daily dose is increased by daily increments is at least 6 days.

18. A method according to claim 2, further comprising continuing to treat said patient by administering the same daily dose as at which clinically efficacy is achieved or reducing said daily dose by daily increments to a lower level at which efficacy can be maintained.

19. A method of treating a patient suffering from bipolar disorder comprising administering to said patient an initial daily dose of 100–800 mg of carbamazepine in extended release form and increasing said dose by daily increments until a final daily dose of 1,000–1,600 mg.

20. A method according to claim 19, wherein said initial daily dose is 100–400 mg.

21. A method according to claim 19, wherein said final daily dose is 1,200–1,600 mg.

22. A method according to claim 21, wherein said final daily dose is 1,200–1,400 mg.

23. A method according to claim 19, wherein said initial daily dose is 200 mg.

24. A method according to claim 21, wherein said initial daily dose is 200 mg.

25. A method according to claim 22, wherein said initial daily dose is 200 mg.

26. A method according to claim 19, wherein said initial daily dose is 400 mg.

27. A method according to claim 21, wherein said initial daily dose is 400 mg.

28. A method according to claim 22, wherein said initial daily dose is 400 mg.

29. A method according to claim 1, wherein the period of time during which the daily dose is increased by daily increments is at least 5 days.

30. A method according to claim 2, wherein the period of time during which the daily dose is increased by daily increments is at least 5 days.

31. A method according to claim 19, wherein the period of time during which the daily dose is increased by daily increments is at least 5 days.

32. A method according to claim 1, wherein carbamazepine is administered twice daily, the initial daily dose is 400 mg, and the daily dose increment is 200 mg.

33. A method according to claim 2, wherein carbamazepine is administered twice daily, the initial daily dose is 400 mg, and the daily dose increment is 200 mg.

34. A method according to claim 19, wherein carbamazepine is administered twice daily, the initial daily dose is 400 mg, and the daily dose increment is 200 mg.

* * * * *